United States Patent
Sofranko et al.

(10) Patent No.: US 11,046,626 B2
(45) Date of Patent: *Jun. 29, 2021

(54) METHODS AND SYSTEMS FOR OXIDATIVE DEHYDROGENATION OF HYDROCARBONS TO OLEFINS

(71) Applicant: EcoCatalytic Inc., Woburn, MA (US)

(72) Inventors: John A. Sofranko, Weston, MA (US); Elena Y. Chung, Somerville, MA (US)

(73) Assignee: EcoCatalytic Inc., Woburn, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/612,256

(22) PCT Filed: May 9, 2018

(86) PCT No.: PCT/US2018/031789
§ 371 (c)(1),
(2) Date: Nov. 8, 2019

(87) PCT Pub. No.: WO2018/208907
PCT Pub. Date: Nov. 15, 2018

(65) Prior Publication Data
US 2020/0123084 A1    Apr. 23, 2020

Related U.S. Application Data

(60) Provisional application No. 62/504,239, filed on May 10, 2017.

(51) Int. Cl.
*C07C 5/42* (2006.01)
*C07C 5/48* (2006.01)
*B01J 19/24* (2006.01)

(52) U.S. Cl.
CPC .............. *C07C 5/42* (2013.01); *B01J 19/2455* (2013.01)

(58) Field of Classification Search
None
See application file for complete search history.

(56) References Cited

U.S. PATENT DOCUMENTS

| 4,554,395 A | 11/1985 | Jones et al. |
| 4,788,372 A | 11/1988 | Gaffney |

(Continued)

FOREIGN PATENT DOCUMENTS

WO    2016049144 A9    3/2016

OTHER PUBLICATIONS

International Search Report and Written Opinion for International Application No. PCT/US2018/031789, dated Jul. 9, 2018, 6 pages.

(Continued)

*Primary Examiner* — Philip Y Louie
(74) *Attorney, Agent, or Firm* — RatnerPrestia (57) ABSTRACT

A method is provided for producing at least one olefin by oxidative dehydrogenation of a hydrocarbon feed. The method includes the steps of contacting a hydrocarbon feed, which includes at least one alkane, and a steam feed with an oxygen transfer agent under a pressure of 1.1 bar to 800 bar to produce at least one olefin. The oxygen transfer agent contains a metal oxide that acts as an oxidizing agent to oxidize the at least one alkane. Additionally, the method includes the step of collecting a product stream containing the at least one olefin.

6 Claims, 8 Drawing Sheets

(56) References Cited

U.S. PATENT DOCUMENTS

| | | | |
|---|---|---|---|
| 4,876,409 A | 10/1989 | Leyshon et al. | |
| 4,886,932 A | 12/1989 | Leyshon | |
| 6,518,476 B1 | 2/2003 | Culp et al. | |
| 2003/0181325 A1* | 9/2003 | Ou | B01J 23/002 502/302 |
| 2004/0068148 A1* | 4/2004 | Allison | B01J 23/56 585/16 |
| 2008/0177117 A1 | 7/2008 | Benderly et al. | |
| 2017/0226030 A1 | 8/2017 | Li et al. | |
| 2017/0247803 A1 | 8/2017 | Sofranko | |
| 2019/0055178 A1* | 2/2019 | Weiss | C07C 5/48 |

OTHER PUBLICATIONS

Neal et al., "On the Mechanistic Aspects of $Mg_6MnO_8$-Based Redox Catalysts for Oxidative Dehydrogenation of Ethane via a Chemical Looping Scheme", AIChE 2016 Annual Meeting, 2016, 23 pages.
International Preliminary Report on Patentability for International Application No. PCT/US2018/031789, dated Nov. 12, 2019, 6 pages.

* cited by examiner

METHODS AND SYSTEMS FOR OXIDATIVE DEHYDROGENATION OF HYDROCARBONS TO OLEFINS

CROSS-REFERENCE TO RELATED APPLICATIONS

This application is a U.S. National Phase Patent Application of PCT Application No. PCT/US2018/031789, filed May 9, 2018, which claims priority to U.S. Provisional Application No. 62/504,239 filed May 10, 2017, the content of each of the aforementioned applications being incorporated by reference herein in its entirety for all purposes.

FIELD OF THE INVENTION

The invention relates to oxygen transfer agents and the reactor systems and processes that utilize the oxygen transfer agents for the oxidative dehydrogenation of hydrocarbons.

BACKGROUND OF THE INVENTION

Ethylene and propylene are important building blocks for the petrochemical industry. These olefins are used in the manufacturing of polymers such as polyethylene, polypropylene, polystyrene and many more chemicals of commercial interest. Over 90% of the global olefin production comes from the high temperature steam cracking of naphtha or ethane and propane. The steam cracking process, which utilizes furnaces, is highly energy intensive, and 1.5 to 2 tons of carbon dioxide is produced for every ton of olefin product.

Natural gas production from shale deposits has dramatically increased supply in recent years. As a result of the continued global demand for olefins and the potential for a new growing supply of ethane and propane available in natural gas liquids from shale deposits, a significant amount of interest and investment is currently centered around expanding the capacity of ethylene and propylene derived from these new sources. Numerous olefin grass root and expansion projects are either under contract or in the planning stages to take advantage of the relative low cost liquids from wet shale gas. However, there are many environmental and cost challenges to bringing on this level of new capacity.

Olefin production is the largest emitter of $CO_2$ and $NO_x$ in the organic chemical industry. With worldwide ethylene production at ~150 MT/yr, the industry emits 150-300 MT/yr of $CO_2$ and roughly 1.4 MT/yr of $NO_x$. Projects located in severe EPA non-attainment zones are challenged by the increase cost of $NO_x$ control. The total greenhouse gas (GHG) emission profile, reported in $CO_2$ equivalents, is another critical part of the permitting for all production expansions.

The industry continues to push for production technology that: (1) generates higher overall yield of ethylene and propylene; (2) increases the run length between furnace turnarounds (e.g. inspections, repairs, improvements, etc.); (3) lowers steam and energy utilization; (4) lowers all GHGs including carbon dioxide and $NO_x$.

The oxidative dehydrogenation of ethane and propane to olefins offers a production route that can significantly reduce $CO_2$ emissions and virtually eliminate $NO_x$ emissions from world scale plants. Oxidative dehydrogenation is a selective catalytic process that produces primarily ethylene and water as products, and is thereby an exothermic reaction (Reaction A).

$$CH_3CH_3 + \tfrac{1}{2}O_2 \rightarrow CH_2CH_2 + H_2O \; \Delta H_o = -105 \text{ kJ/mol} \quad \text{Reaction (A)}$$

The per pass yield of the oxidative dehydrogenation reaction is not limited by thermodynamic equilibrium, as it is in pyrolysis (Reaction B).

$$CH_3CH_3 + \text{Heat} \leftrightarrows CH_2CH_2 + H_2 \; \Delta H_o = +137 \text{ kJ/mol} \quad \text{Reaction (B)}$$

Oxidative dehydrogenation provides an opportunity to achieve some of the objectives to improve the efficiency of olefin production. There is a need for materials for facilitating oxidative dehydrogenation, as well as reactors and processes that include these improved materials.

SUMMARY OF THE INVENTION

Aspects of the present invention are directed to methods, systems, and apparatuses for producing olefins by oxidative dehydrogenation of a hydrocarbon feed.

In accordance with one aspect of the invention, a method is provided for producing at least one olefin by oxidative dehydrogenation of a hydrocarbon feed. The method includes the steps of contacting a hydrocarbon feed comprising at least one alkane and a steam feed with an oxygen transfer agent under a pressure of 1.1 bar to 800 bar to produce at least one olefin. The oxygen transfer agent comprises a metal oxide that acts as an oxidizing agent to oxidize the at least one alkane. Additionally, the method includes the step of collecting a product stream comprising the at least one olefin.

According to another aspect of the invention, a system is provided for producing at least one olefin by oxidative dehydrogenation of a hydrocarbon feed. The system includes a hydrocarbon feed comprising at least one alkane; a steam feed comprising steam; and a reactor containing an oxygen transfer agent therein. The oxygen transfer agent comprises a metal oxide that acts as an oxidizing agent to oxidize the at least one alkane and is configured to produce at least one olefin from the at least one alkane by oxidative dehydrogenation. The reactor operates under a pressure of 1.1 bar to 800 bar.

Various aspects of the invention may be summarized as follows:

Aspect 1: A method for producing one or more olefins from a hydrocarbon feed comprised of one or more alkanes, the method comprising:
contacting a hydrocarbon feed comprising at least one alkane and a steam feed with an oxygen transfer agent under a pressure of 1.1 bar to 800 bar to produce at least one olefin, the oxygen transfer agent comprising a metal oxide that acts as an oxidizing agent to oxidize the at least one alkane; and
collecting a product stream comprising the at least one olefin.

Aspect 2: The method of Aspect 1, wherein an increase in the pressure increases the selectivity for olefins.

Aspect 3: The method of Aspect 1, wherein during the contacting step the hydrocarbon feed has a temperature of 100° C. to 1100° C.

Aspect 4: The method of Aspect 3, wherein during the contacting step the hydrocarbon feed has a temperature of 550° C. to 950° C.

Aspect 5: The method of Aspect 3, wherein during the contacting step the hydrocarbon feed has a temperature of 800° C. to 850° C.

Aspect 6: The method of Aspect 1, wherein the metal oxide comprises at least one element selected from the group consisting of Na, Li, Ca, Mg, Sr, P, and Ba.

Aspect 7: The method of Aspect 1, wherein the metal oxide comprises at least one element selected from the group consisting of La, Ce, Pr, Tb, Nd, Mn, W, Ti, Fe, and Dy.

Aspect 8: The method of Aspect 1, wherein the metal oxide is in combination with a zeolite.

Aspect 9: A system for producing one or more olefins from a hydrocarbon feed comprised of one or more alkanes comprising:

a first feed line containing a hydrocarbon feed comprising at least one alkane; and a second feed line containing a steam feed comprising steam;

a reactor containing an oxygen transfer agent therein, the oxygen transfer agent comprising a metal oxide that acts as an oxidizing agent to oxidize the at least one alkane and configured to produce at least one olefin from the at least one alkane by oxidative dehydrogenation, the reactor operating under a pressure of 1.1 bar to 800 bar, wherein the first feed line and the second feed line are fluidly connected, directly or indirectly to the reactor.

Aspect 10: The system of Aspect 9, wherein the reactor comprises a fixed bed or a fluid bed containing the oxygen transfer agent.

Aspect 11: The system of Aspect 9, wherein the reactor is a chemical looping reactor.

Aspect 12: The system of Aspect 9, further comprising a recycle stream, the recycle stream comprising unreacted alkanes from the hydrocarbon feed.

BRIEF DESCRIPTION OF THE FIGURES

The invention is best understood from the following detailed description when read in connection with the accompanying drawings, with like elements having the same reference numerals. Included in the drawings are the following figures.

DETAILED DESCRIPTION OF THE INVENTION

In the following detailed description, numerous specific details are set forth by way of examples in order to provide an understanding of the relevant teachings. However, it should be apparent to those skilled in the art that the present teachings may be practiced without such details. In other instances, well known methods, procedures, compounds, and process units have been described at a relatively high-level, without detail, in order to avoid unnecessarily obscuring aspects of the present teachings.

Figure 1:
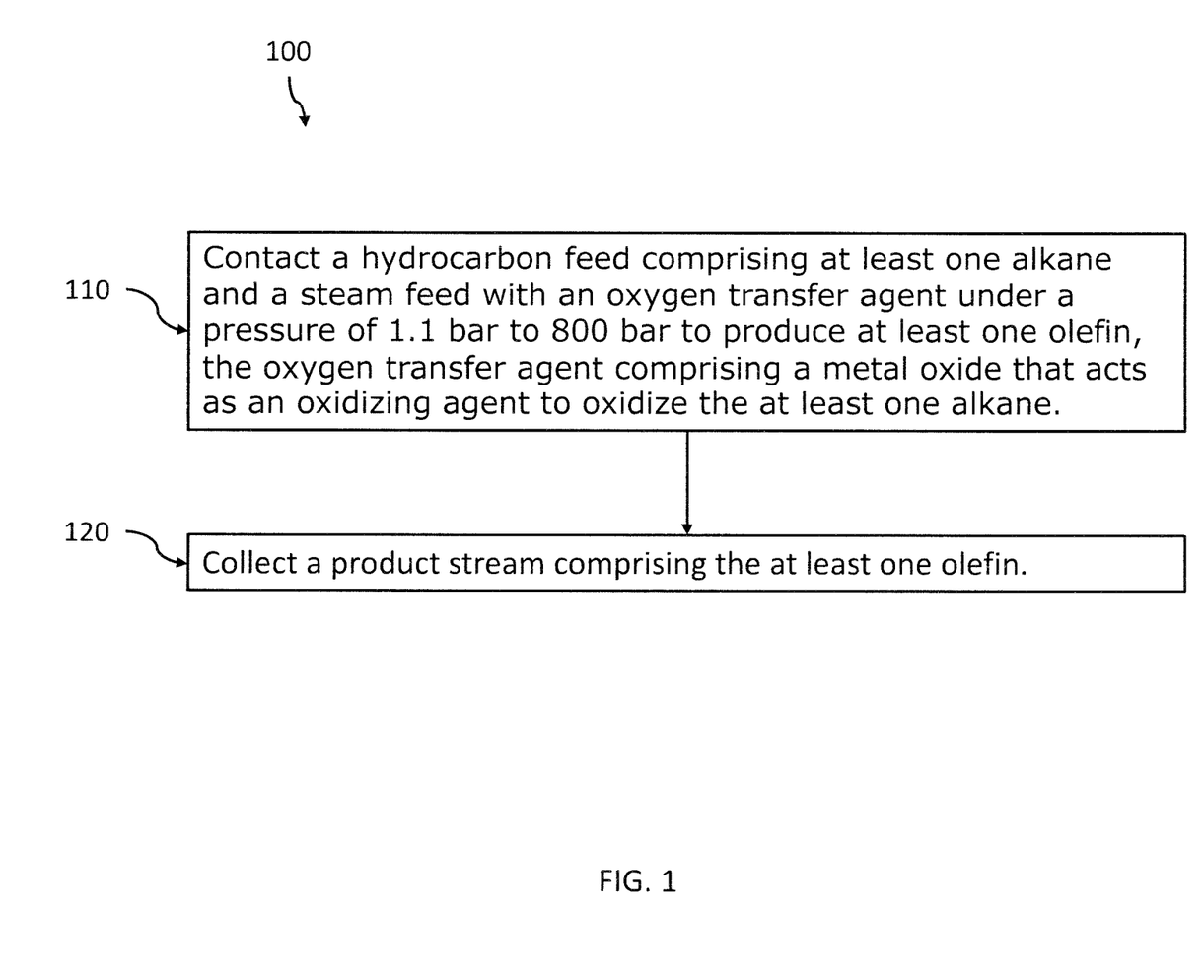
FIG. 1 illustrates a method for producing at least one olefin from a hydrocarbon feed comprising at least one alkane in accordance with aspects of the invention.

FIG. 1 illustrates an exemplary method 100 for producing at least one olefin from a hydrocarbon feed comprising at least one alkane. The at least one olefin may be produced by oxidative dehydrogenation of the at least one alkane of the hydrocarbon feed. Oxidative dehydrogenation mechanisms occur according to the following generalized formula of Equation 1:

$$zC_nH_{2n+2-2\beta}+(z-1+\delta)\text{"O"} \rightarrow C_{(z \times n)}H_{2(z \times n)+2-2\beta-2\delta}+(z-1+\delta)H_2O \qquad \text{(Eq. 1)}$$

where z=the number of reacting molecules; n=the number of carbon atoms in the reacting molecule; β=the degree of unsaturation where the value is zero for single bonds, one for double bonds and molecular rings, and two for triple bonds; and δ=the change in the degree of unsaturation.

In step 110, a hydrocarbon feed comprising at least one alkane and a steam feed are contacted with an oxygen transfer agent under a pressure of 1.1 bar to 800 bar to produce at least one olefin. The hydrocarbon feed may, for example, include one or more aliphatic hydrocarbons (alkanes), such as methane, ethane, propane, butane, hexane, heptane, octane, etc. According to a particularly preferred embodiment, the hydrocarbon feed includes one or more alkanes containing two or more carbon atoms (e.g., $C_2$-$C_8$ alkanes), which may be straight chain and/or branched in structure. Substances other than alkanes may also be present in the hydrocarbon feed. The hydrocarbon feed may be derived from natural gas obtained from unconventional well drilling techniques and/or crude oil or gas obtained from traditional well drilling techniques. For example, the hydrocarbon feed may be natural gas. In one embodiment, the hydrocarbon feed includes alkanes obtained from natural gas, such as methane and ethane. In another embodiment, however, the hydrocarbon feed may include an insignificant amount of methane, such as 5%, by weight, or less; or 2%, by weight, or less; or 1%, by weight, or less of methane. The hydrocarbon feed may include at least 30% ethane by weight, preferably at least 40% ethane by weight, preferably at least 50% ethane by weight, preferably at least 60% ethane by weight, preferably at least 70% ethane by weight, preferably at least 80% ethane by weight, or preferably at least 90% ethane by weight. In one embodiment, the hydrocarbon feed consists of ethane and impurities. It is also contemplated herein that one or more alkanes of the hydrocarbon feed stream may be derived from a renewable resource, such as algae, plant materials, etc.

The steam feed comprises water in a vapor phase. Although the steam feed may consist essentially of $H_2O$ molecules, embodiments of the invention may include impurities and/or other substances in the steam feed. The steam feed may include low levels of molecular oxygen, such as 10% or less by volume, to reduce the risk of combustion. Additionally and/or alternatively, the steam feed may include inert gases at amounts that reduce the risk of combustion. The steam feed may be adapted to have a temperature such that the steam remains in the vapor phase under increased pressures of the reactor or after various unit processes. The steam feed may have a temperature of 100.6° C. or more, 102° C. or more, 110° C. or more, 152° C. or more, 170° C. or more, 180° C. or more, 200° C. or more, 250° C. or more, 300° C. or more, 400° C. or more, 500° C. or more, 600° C. or more, 800° C. or more, or 1000° C. or more. The steam feed may be super-heated steam or saturated steam. It should be understood that the steam feed and the hydrocarbon feed may, in various embodiments of the invention, may be combined to flow through a single feed pipe and/or inlet prior to entering the reactor and/or contacting the oxygen transfer agent contained therein. The steam feed may be employed in an amount effective to provide a molar ratio of water (contributed by the steam feed) to the hydrocarbon feed of 1:10 to 10:1. For example, the molar ratio of water (contributed by the steam feed) to the hydrocarbon feed may be 2:9 to 9:2, 3:7 to 7:3, or 4:6 to 6:4.

The oxygen transfer agent includes at least one metal oxide that acts as an oxidizing agent to oxidize the at least one alkane (i.e., the metal oxide is a reducible metal oxide). The metal oxide comprises oxygen ("O") and at least one metal, preferably at least one alkali metal or alkali earth metal. One or more transition metals may also be present in the metal oxide. For example, the oxygen transfer agent may include a metal oxide comprising titanium ("Ti"), lithium ("Li"), lanthanum ("La"), cerium ("Ce"), zinc ("Zn"), copper ("Cu"), vanadium ("V"), manganese ("Mn"), praseodymium ("Pr"), neodymiun ("Nd"), dysprosium ("Dy"), tungsten ("W"), iron ("Fe") terbium ("Tb"), and/or any compound thereof. In one embodiment, the metal oxide may be formed from one or more elements selected from the group consisting of Mn, Li, and Mg. In another embodiment, the metal oxide comprises at least one element selected from the group consisting of La, Ce, Pr, Tb, Nd, Mn, W, Ti, Fe, and Dy. Preferably, the reducible metal oxide comprises a manganese oxide having a valence state of 4+, 3+, 8/3+, or 2+. For example, the reducible metal oxide may comprise: a) at least one compound selected from the group consisting of $NaB_2Mg_4Mn_2O_4$, $NaB_2Mn_2Mg_4O_{11.5}$, $NaMn_2O_4$, $LiMn_2O_4$, $Mg_3Mn_3B_2O_{10}$, $Mg_3(BO_3)_2$, and b) a non-crystalline compound comprising oxygen and at least one of sodium ("Na"), boron ("B"), Mg, Mn, or Li. In addition to being reducible, the metal oxide may be ionically and electronically conductive. Additionally and/or alternatively, the oxygen transfer agent may also include a small amount of B to increase the toughness of the metal oxide particles and/or the structure of the oxygen transfer agent.

The oxygen transfer agent may be comprised of at least 0.5% by weight metal oxide(s) and up to 100% by weight metal oxide(s). For example, the oxygen transfer agent may comprise an amount, by weight, of metal oxide ranging from 5% to 95%; preferably 15% to 90%; more preferably 20% to 85%; more preferably 25% to 80%; more preferably 30% to 75%; more preferably 35% to 70%; and/or more preferably 40% to 65%. Additionally and/or alternatively, the oxygen transfer agent may comprise an amount of metal oxide, by weight, ranging from 0.5% to 10%; 10% to 20%; 20% to 30%; 30% to 40%; 40% to 50%; 50% to 60%; 60% to 70%; 70% to 80%; 80% to 90%; or 90% to 100%. Mixtures of different metal oxides may also be utilized. The oxygen transfer agent may include at least one promoter integrally dispersed (e.g., uniformly dispersed) with the metal oxide. In one embodiment, the promoter is selected from the group consisting of Na, calcium ("Ca"), strontium ("Sr"), phosphorous ("P"), and barium ("Ba").

The oxygen transfer agent may also comprise a zeolite that may be configured to accelerate the rate of oxidative dehydrogenation of the hydrocarbon feed. The zeolite may have a composition in accordance with the general formula: $M_{2/n}O \cdot Al_2O_3 \cdot ySiO_2 \cdot wH_2O$ where y is from 2 to 1,000,000, M is a positively charged element for balancing the charge of the zeolite and may include protons, alkaline metals, alkaline earth metals or other elements known to those skilled in the art, n represents the cation valence and w represents the number of water molecules per zeolite unit structure, such that, at least 5% of n are protons. For example, the zeolite may have a composition in accordance with the above general formula where y is from 4 to 35. In one embodiment, the zeolite comprises ZSM-5, while in another embodiment the zeolite is selected from a group consisting of ZSM-5, MCM 22, and MCM 56. Suitable amounts of Bronsted and/or Lewis acids may be utilized to optimize the activity of the zeolites. The molar ratio of the amount of metal oxide(s) to zeolite(s) may range from, e.g., 100:1 to 1:100; 95:5 to 5:95; 90:10 to 10:90; 85:15 to 15:85; 80:20 to 20:80; 75:25 to 25:75; 70:30 to 30:70; 65:35 to 35:65; 60:40 to 40:60; and/or 55:45 to 45:55. Additionally and/or alternatively, the molar ratio of the amount of metal oxide(s) to zeolite(s) may range from ranging from 95:5 to 90:10; 90:10 to 85:15; 85:15 to 80:20; 80:20 to 75:25; 75:25 to 70:30; 70:30 to 65:35; 65:35 to 60:40; 60:40 to 55:45; 55:45 to 50:50; 50:50 to 45:55; 45:55 to 40:60; 40:60 to 35:65; 35:65 to 30:70; 30:70 to 25:75; 25:75 to 20:80; 20:80 to 15:85; 15:85 to 10:90; or 10:90 to 5:95.

The oxygen transfer agents disclosed herein may be prepared by any methods known by those skilled in the art, including, but not limited to, precipitation, co-precipitation, impregnation, granulation, spray drying, dry mixing, etc. Precursors may be transformed into active agents by calcination at temperatures suitable for the formation of the active components, e.g., in the range of 400° to 1,100° C. The calcination may be performed under any atmosphere, such as air, inert gases, hydrogen, carbon monoxide, and hydrocarbon gases, so as to form the active oxygen transfer agents of the present invention. The oxygen transfer agent may be admixed or otherwise formulated with binders, supports, carriers and the like using any conventional procedures known in the art and may be utilized in any suitable shape or physical form such as powder, granules, pellets, beads, rings, monoliths, extrudates and the like. Suitable oxygen transfer agents and methods of manufacturing the same may be found in PCT Patent Publication No. WO 2018/005456, which is incorporated herein in its entirety for all purposes.

The hydrocarbon feed and steam feed are brought into contact with the oxygen transfer agent under a pressure of 1.1 bar to 800 bar. The inventors discovered that the conversion of the at least one alkane, and particularly ethane conversion, to olefins was increased by an increase in the pressure applied during the oxidative dehydration of the hydrocarbon feed. Additionally, the inventors discovered that employing a steam feed and increasing the pressure applied during the oxidative dehydration of the hydrogen feed synergistically increases the selectivity to ethylene and other desired olefins. The inventors were surprised by the improved selectivity and conversion of the hydrocarbon feed to desired olefins, such as ethylene and/or propylene, for several reasons. First, the commonly accepted mechanism for the oxidative dehydrogenation of ethane to ethylene using an oxygen transfer agent would indicate inferior/reduced conversion and selectivity to desired olefins as a result of increased pressure. According to the commonly accepted mechanism, ethane is believed to undergo reversible pyrolysis to ethylene and hydrogen, followed by the irreversible oxidation of the transient hydrogen to water, as seen in Equations (1)-(4) below, during oxidative dehydrogenation.

$$CH_3CH_3 \leftrightarrows CH_2CH_2 + H_2 \quad \text{Equation (1)}$$

$$H_2 + MeO_x \rightarrow H_2O + MeO_{x-1} \quad \text{Equation (2)}$$

$$MeO_{x-1} + \tfrac{1}{2}O_2 \rightarrow MeO_x \quad \text{Equation (3)}$$

$$CH_3CH_3 \rightarrow CH_2CH_2 + H_2O \quad \text{Equation (4)}$$

The inventors discovered, however, that applying pressure during the oxidative dehydration of the hydrogen feed favors the rate of Equation (2), which is irreversible over the reverse rate of Equation (1). Further, the inventors discovered that aspects of the invention have an overall rate of ethylene production that increases exponentially with an increased pressure during the oxidative dehydrogenation of ethane.

Second, the inventors discovered that the application of a steam feed during the oxidative dehydrogenation of a hydrocarbon feed improves the selectivity to ethylene and other desired olefins over undesired carbon oxide products synergistically with the increase in pressure. The improved selectivity to ethylene and other desired products from the oxidative dehydrogenation of the hydrocarbon feed due to applied pressure (as discussed above) and the steam feed was surprising. The generally accepted mechanism for the formation of carbon oxide products by way of oxidative dehydration of a hydrocarbon feed is provided below as Equations (5) and (6).

$$CH_2CH_2 + 6MeO_x \rightarrow 2CO_2 + 2H_2O + 6MeO_{x-1} \quad \text{Equation (5)}$$

$$CH_2CH_2 + 4MeO_x \rightarrow 2CO + 2H_2O + 4MeO_{x-1} \quad \text{Equation (6)}$$

Because Equation 2 is irreversible, it is not obvious why the addition of steam should provide any beneficial effect to the selectivity of ethylene selectivity more than the stoichiometric product of water. Without limiting the scope of the invention, the inventors believe that the beneficial effects of employing a steam feed may be explained via a mechanism for non-selective product formation of olefins that proceeds via transient carbon (e.g., coke) formation on the oxygen transfer agent, which is subsequently oxidized very rapidly via oxygen provided by the oxygen transfer agent, as shown in Equations 7-10.

$$CH_2CH_2 \rightarrow Coke + 4H_2 \quad \text{Equation (7)}$$

$$2MeO_x + H_2 \rightarrow H_2O \quad \text{Equation (8)}$$

$$Coke + 2MeO_x \rightarrow CO_2 + 2MeO_{x-1} \quad \text{Equation (9)}$$

$$Coke + MeO_x \rightarrow CO + MeO_{x-1} \quad \text{Equation (10)}$$

Although it may not be surprising that the addition of steam to the ethane pyrolysis feed reduces the rate of coke production, it is surprising that the oxidative dehydration reaction of the hydrocarbon feed promoted in the oxidizing environment of the oxygen transfer agent in the presence of steam has the beneficial effect of increasing the selectivity for desired olefins, such as ethylene, over undesired carbon oxide products. These results contradict the commonly accepted mechanism for the formation of carbon oxides over the desired olefins (e.g., ethylene and/or propylene) by oxidative dehydration of the hydrocarbon feed. The rate of coking is generally thought to increase with an increase in the pressure of the reactor system (e.g., during the oxidative dehydration of the hydrocarbon feed). However, the combination of steam and pressure has a synergistic effect (as shown in the examples below) to increase the selectivity and conversion of the hydrocarbon feed to desired olefins. Additionally, the steam feed may be configured to increase the density of the oxygen transfer particles and improve fluidization and attrition resistance of the oxygen transfer particles.

Method 100 produces at least one olefin as a result of contacting the hydrocarbon feed and steam feed with the oxygen transfer agent under a pressure of 1.1 bar to 800 bar. The oxidative dehydrogenation of the at least one alkane of the hydrocarbon feed, preferably, occurs under a pressure of 1.5 bar to 10 bar, 2 bar to 9 bar, 3 bar to 8 bar, 4 bar to 7 bar, and/or 5 bar to 6 bar. The oxidative dehydrogenation is also contemplated at higher pressures, such as at a pressure of 15 bar to 750 bar, 30 bar to 700 bar, 45 bar to 650 bar, 60 bar to 600 bar, 75 bar to 550 bar, 90 bar to 500 bar, 105 bar to 450 bar, 120 bar to 400 bar, 135 bar to 350 bar, 150 bar to 300 bar, and/or 165 bar to 250 bar. Additionally and/or alternatively, the oxidative dehydrogenation of the at least one alkane may occur under a pressure of 1.1 bar or more, 2 bar or more, 3 bar or more, 4 bar or more, 5 bar or more, 6 bar or more, 7 bar or more, 8 bar or more, 9 bar or more, 10 bar or more, 50 bar or more, 100 bar or more, 150 bar or more, 200 bar or more, 240 bar or more, 260 bar or more, 280 bar or more, 300 bar or more, 360 bar or more, 420 bar or more, etc.

The at least one alkane of the hydrocarbon feed may have a temperature during contacting step 110 of 100° C. to 1100° C., 250° C. to 1050° C., 400° C. to 1000° C., 550° C. to 950° C., and/or 700° C. to 900° C. For example, the at least one alkane may have a temperature during the contacting step of 100° C. or more, 110° C. or more, 120° C. or more, 130° C. or more, 140° C. or more, 150° C. or more, 175° C. or more, 200° C. or more, 225° C. or more, 250° C. or more, 300° C. or more, 350° C. or more, 400° C. or more, 450° C. or more, 500° C. or more, 650° C. or more, 700° C. or more, 800° C. or more, 900° C. or more, or 1000° C. or more. In one embodiment, the at least one alkane has a temperature during the contacting step of 800° C. to 850° C.

Method 100 produces at least one olefin, such as ethylene and/or propylene, and may coproduce $H_2O$. The coproduction of water indicates a desirable selectivity of the oxygen transfer agent, favoring reaction mechanisms that produce water instead of hydrogen gas. For example, large amounts of water coproduction may indicate that the oxygen transfer agent has a high selectivity for donating an oxygen atom to the hydrocarbon feed molecules, which facilitates removal of hydrogen atoms from the hydrocarbon feed molecule and, thereby, supports oxidative dehydration. Thus, the co-product water is preferably formed from oxygen donated by the oxygen transfer agent. For example, in one embodiment, at least 49% by mole of the hydrocarbon feed is converted to oxides of carbon, whereby water is produced as a co-product. In another embodiment, at least 49% by mole of the hydrocarbon feed is converted to olefins, whereby water is produced as a co-product. Preferably, method 100 produces more water than hydrogen on a molar basis. For example, the molar ratio of water to hydrogen may be at least 1:1, preferably at least 2:1, preferably at least 3:1, preferably at least 4:1, preferably at least 5:1, preferably at least 6:1, preferably at least 7:1, preferably at least 8:1, preferably at least 9:1, preferably at least 10:1, preferably at least 11:1, preferably at least 12:1, or preferably at least 13:1.

In step 120, a product stream comprising at least one olefin is collected. The product of the oxidative dehydration of the hydrocarbon feed may comprise olefins at 30% or more, preferably 35% or more, preferably 40% or more, preferably 45% or more, preferably 50% or more, preferably 52% or more, preferably 55% or more, preferably 58% or more, preferably 60% or more, preferably 65% or more, preferably 70% or more, preferably 75% or more, preferably 80% or more, preferably 85% or more, preferably 90% or more, or preferably 95% or more, by weight. The composition of the olefins may include ethylene, propylene, or a combination thereof in an amount of 30% or more, preferably 35% or more, preferably 40% or more, preferably 45% or more, preferably 50% or more, preferably 55% or more, preferably 58% or more, preferably 60% or more, preferably 62% or more, preferably 64% or more, preferably 66% or more, preferably 68% or more, preferably 70%, preferably 72% or more, preferably 74% or more, preferably 76% or more, preferably 78% or more, preferably 80% or more, preferably 82% or more, preferably 84% or more, preferably 86% or more, or preferably 88% or more, by weight.

The product collected in step 120 may be further fractionated, purified, recycled, converted, etc. For example, the product may purified downstream in order to isolate polymer grade olefins. For example, ethylene fractionation may include one or more driers in order to remove water prior to feeding the dried product to a distillation column. The polymer grade olefins may then be sold as raw materials for the production of higher molecular weight products by oligomerization. Numerous catalysts and processes are known for the oligomerization of olefins generally, and of ethylene particularly, all of which may be employed for converting the polymer grade olefins made according to the various methods of the present invention to higher molecular weight products. For example, phosphoric acid supported on a kieselguhr base has been widely used for making polymer gasoline (i.e., olefinic hydrocarbon liquids within the gasoline boiling range) from refinery gases. Other catalysts which have been employed for similar purposes include the oxides of cobalt, nickel, chromium, molybdenum and tungsten on supports such as alumina, silica-alumina, kieselguhr, carbon and the like. Higher hydrocarbon products of interest may include aviation fuels, kerosene, or intermediate refining streams. Examples of suitable catalysts for oligomerization of olefins may be found in PCT Publication no. WO 2016/049144, which is incorporated herein in its entirety for all purposes.

Figure 2:
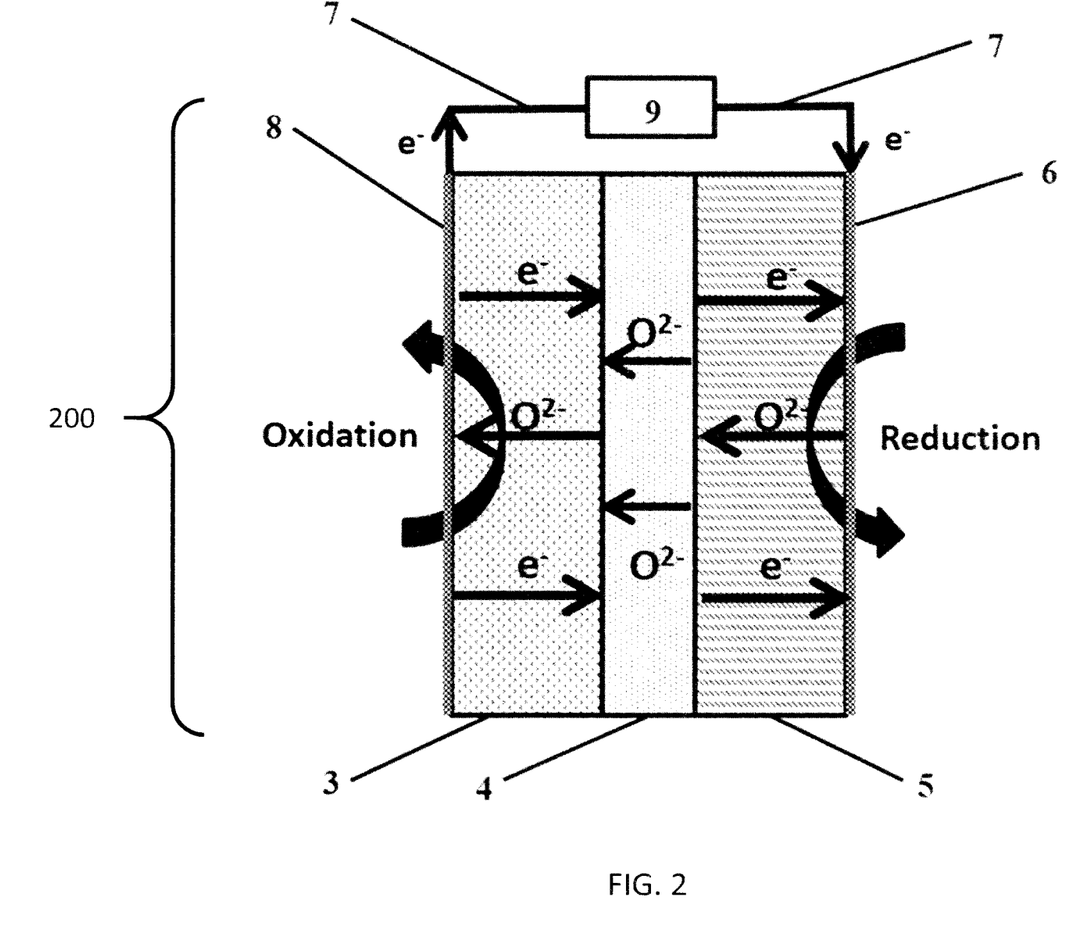
FIG. 2 is a schematic block diagram of an exemplary electro-generative reactor according to an aspect of the invention.
Figure 3:
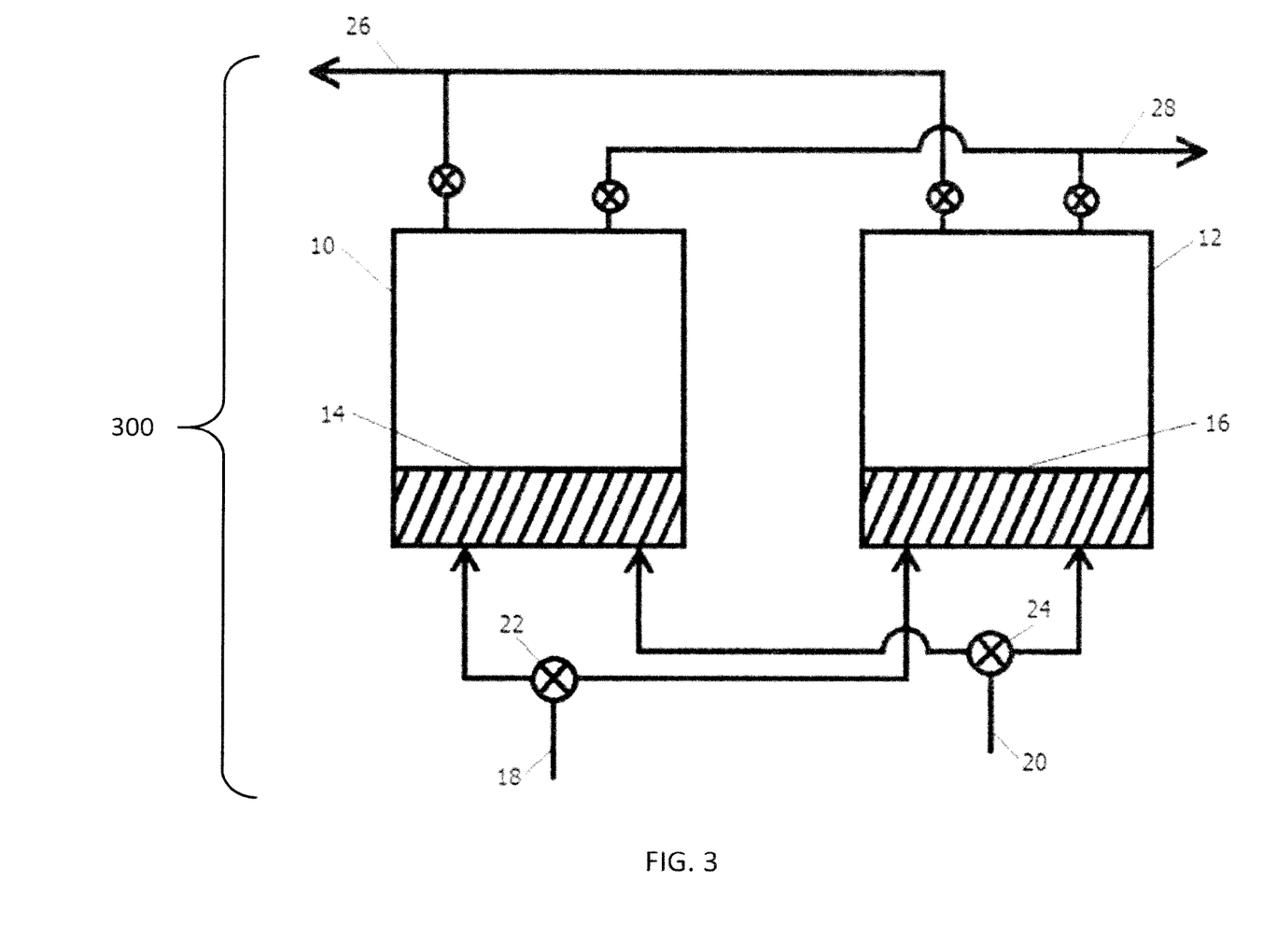
FIG. 3 illustrates a schematic of an exemplary system comprising two fixed-bed reactors for producing at least one olefin from a hydrocarbon feed in accordance with aspects of the invention.
Figure 4:
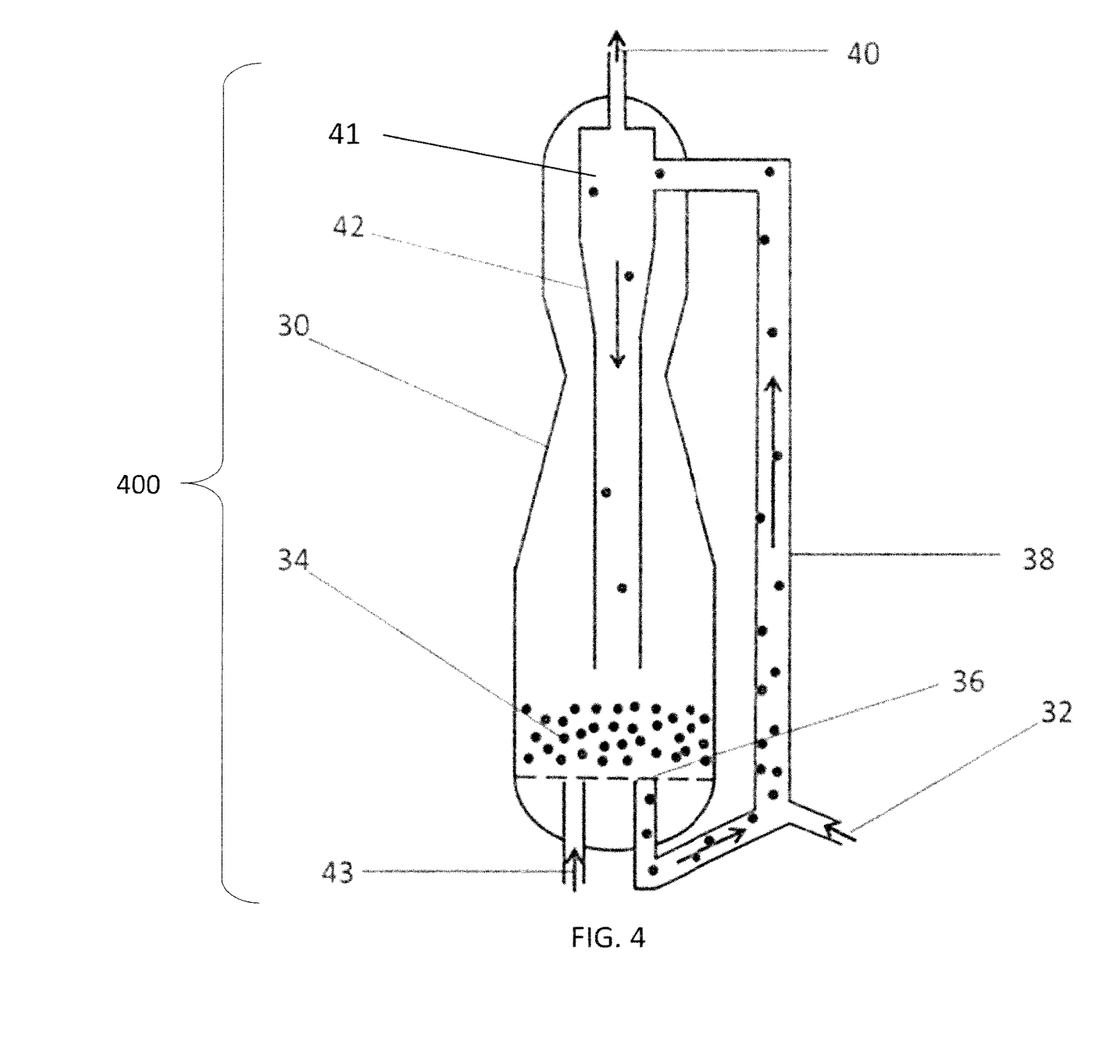
FIG. 4 illustrates a schematic of an exemplary system comprising a fluid bed reactor and at least one cyclone system for producing at least one olefin from a hydrocarbon feed according to an aspect of the invention.

FIGS. 2-4 are schematics of exemplary, non-limiting systems 200, 300, and 400 for producing olefins from a hydrocarbon feed comprising at least one alkane. Systems 200, 300, and 400 may employ various aspects of the methods, such as method 100, discussed above. As a general overview, systems 200, 300, and 400 include a hydrocarbon feed comprising at least one alkane, a steam feed comprising steam, and a reactor containing an oxygen transfer agent therein. The oxygen transfer agent comprises a metal oxide that acts as an oxidizing agent to oxidize the at least one alkane and is configured to produce at least one olefin from the at least one alkane by oxidative dehydrogenation. The reactor operates under a pressure of at least 1.1 bar.

FIG. 2 is a schematic block diagram of an electro-generative reactor 200 according to aspects of the invention. An electro-generative reactor utilizes favorable thermodynamics and kinetic factors in an electrochemical cell to generate byproduct electricity while bringing about a desired reaction. In one embodiment, the electro-generative reactor is a fuel cell that produces olefins and electricity. The amount of electricity produced may be optimized by varying the production ratio of products, such as olefins, water, $CO_2$, electricity, etc.

Reactor 200 includes an oxidation zone 3, a reduction zone 5, an electron barrier 4 disposed between oxidation zone 3 and reduction zone 5, and a conductor 7 attached to oxidation zone 3 and reduction zone 5. The oxidation zone 3 includes an oxygen transfer agent. The oxidation zone 3 is configured to oxidize the at least one alkane of the hydrocarbon feed, in the presence of steam provided by the steam feed. The oxidation zone 3 may be comprised of mixed conductive materials, thereby conducting oxygen anions and also having electronic conductivity. The reduction zone 5 is configured to reduce an oxygen-containing compound to anionic oxygen. The electron barrier 4 may be configured to allow transmission of the anionic oxygen from reduction zone 5 to oxidation zone 3 and to resist transmission of electrons from the oxidation zone 3 to the reduction zone 5. Conductor 7 is configured to conduct electrons from the oxidation zone 3 to the reduction zone 5.

Additionally and/or alternatively, power 9 may be applied through conductor 7 to a reduction zone 5, which promotes the reduction of oxygen to oxygen anion in the cathode plate 6. However, in one embodiment, power is removed from the electro-generative fuel cell by way of conductor 7. The oxidation of the hydrocarbon feed stream occurs in the oxidation zone 3 and electrons are conducted through an anode plate 8 to complete the power circuit. Oxygen anions move through the electron barrier 4, which is intimately associated with the selective oxygen transfer agent in the oxidation zone 3. In this oxygen pumping embodiment, the effective pressure differential of oxygen between the reduction membrane and oxidation membrane is increased, thereby increasing the rate of oxygen anion transfer through the electron barrier. Suitable examples of electro-generative reactors and fuel cells may be found in U.S. Patent Publication No. US 2017/0247803, which is incorporated herein in its entirety for all purposes.

FIG. 3 illustrates a schematic of a non-limiting, exemplary system 300 comprising two fixed-bed reactors 10, 12. In the case of fixed bed reactors, multiple reactors may be used such that oxidative dehydrogenation and the re-oxidation of the oxygen transfer agent are occurring continuously as feed and air are alternately cycled to multiple reactors, such as system 300 illustrated in FIG. 3. The two fixed-bed reactors 10, 12 may each contain a layer of oxygen transfer agent 14, 16. A hydrocarbon feed line 18 for delivering a hydrocarbon feed, such as ethane, may include a valve 22 to selectively direct the hydrocarbon feed to either the first reactor 10 or the second reactor 12. A steam feed line (not shown) for delivering a steam feed may include a valve to selectively direct the steam feed to either the first reactor 10 or the second reactor 12. If the first reactor 10 is selected, the hydrocarbon and steam will pass through the layer of oxygen transfer agent 14, which promotes an oxidative dehydrogenation reaction, resulting in a product stream containing an unsaturated hydrocarbon, such as ethylene, and water that exits the first effluent line 26. During this process in the first reactor 10, the oxygen transfer agent 14 is reduced over time. In order to regenerate the agent, the feed stream is diverted through valve 22 to the second fixed bed reactor 12, and an oxygen-containing gas stream, such as air, from feed line 20 is fed through valve 24 to the first reactor 10. The oxygen-containing gas oxidizes the oxygen transfer agent 14, and the oxygen-depleted product gas exits effluent stream 28. As the oxygen transfer agent 14 in the first reactor 10 is being regenerated through oxidation, the second reactor 12 is producing at least one olefin and, optionally, water that exits effluent stream 26. Upon reaching the point where regeneration of the oxygen transfer agent 16 in the second reactor 12 is desired, the hydrocarbon feed and oxygen containing gas feeds may be switched using the valves 22, 24, with the steam feed also being switched. This arrangement provides a continuous production of unsaturated hydrocarbon, as well as continuous oxygen transfer agent regeneration. Suitable examples of fixed bed reactors and fluid bed reactors may be found in PCT Patent Publication No. WO 2016/049144, which is incorporated herein in its entirety for all purposes.

FIG. 4 illustrates a schematic of a non-limiting, exemplary system 400 comprising a fluid bed reactor 30 and at least one cyclone system 41. The reactor of system 400 may consist of a single riser. Although system 400 is illustrated in FIG. 4 as having a single riser, system 400 may be configured to have two or more risers. System 400 includes a hydrocarbon feed stream 32, such as ethane, that is fed to the hydrocarbon reaction section 38 of reactor 30. System 400 also includes a steam feed (not shown) that is also fed to the hydrocarbon reaction section 38 of reactor 30. Also fed to the hydrocarbon reaction section 38 of reactor 30 is an oxygen transfer agent from bed 34 through an outlet 36 underneath the bed 34. The hydrocarbon feed, steam feed and the oxygen transfer agent travel together vertically upwards through the height of the reaction section 38. Although the hydrocarbon feed, steam feed and oxygen transfer agent travel vertically through the reaction section in FIG. 4, in other embodiments of the invention, the oxygen transfer agent flows vertically downwards and the hydrocarbon feed and steam feed flow counter-currently downwards or co-currently upwards. As would be understood by those of skill in the art, the flow rate of reactants and dimensions of the reaction zone 38 may be optimized to maximize the reaction rate for the production of unsaturated hydrocarbons, such as ethylene. The reduced oxygen transfer agent may then returned to the bed 34 via an internal return line 42, while the unsaturated hydrocarbon product exits reactor 30 via an outlet 40. In order to regenerate the oxygen transfer agent, an oxygen-containing gas, such as air, is fed through a second inlet 43 to the bottom of the bed 34. Any oxygen-depleted gas exiting the top of the bed 34 may also exit through the outlet 40 with the product stream.

Figure 8:
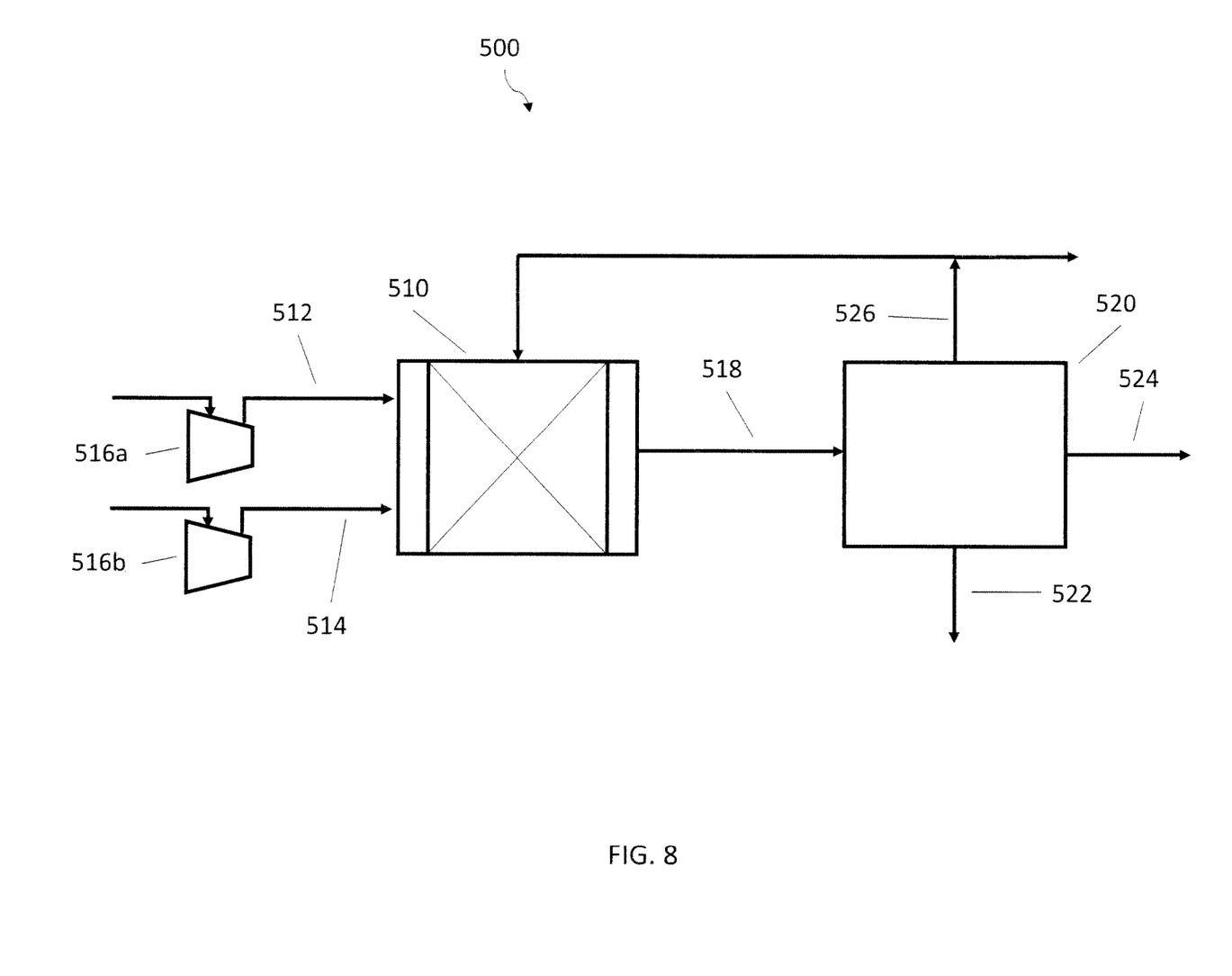
FIG. 8 illustrates a schematic of a non-limiting, exemplary system that includes a recycle stream adapted for recycling unreacted alkanes.

FIG. 8 illustrates a schematic of a non-limiting, exemplary system 500 that includes a recycle stream adapted for recycling unreacted alkanes. As a general overview, system 500 includes a reactor 510 and a separation unit 520.

Reactor 510 may be a batch reactor, a fluid bed reactor, a fixed bed reactor, an electro-generative reactor, or the like. Reactor 510 is in fluid communication with first feed stream 512, which comprises a hydrocarbon feed of at least one alkane, and with second feed stream 514, which comprises a steam feed. Although first feed stream 512 and second feed stream 514 are connected to reactor 510 using separate pipes in FIG. 8, in alternative embodiments first feed stream 512 and the second feed stream 514 are supplied to reactor 510 using a single pipe. Compressors 516a and 516b are in fluid communication with first feed stream 512 and second feed stream 514, respectively, to supply the hydrocarbon feed and steam to reactor 510 and/or to increase the pressure within reactor 510. Reactor outlet stream 518 is adapted transfer the output of reactor 510 to separation unit 520.

Separation unit 520 is configured to separate the at least one olefin, unreacted alkanes, steam, and/or any byproducts. Although separation unit 520 is schematically illustrated in FIG. 8 as a single processing unit, it should be understood that separation unit 520 may comprise one or more processing units for separating and/or isolating components of the reactor outlet stream 518 from reactor 510. Separation unit 520 may be configured to provide a heavy stream 522 comprising water and other heavy products for further processing, a product stream 524 comprising at least one olefin, and a recycle stream 526 for recycling at least unreacted alkanes.

EXAMPLES

The following examples are included herein to demonstrate the advantageous utility obtained from aspects of the present invention.

Example 1

Figure 5:
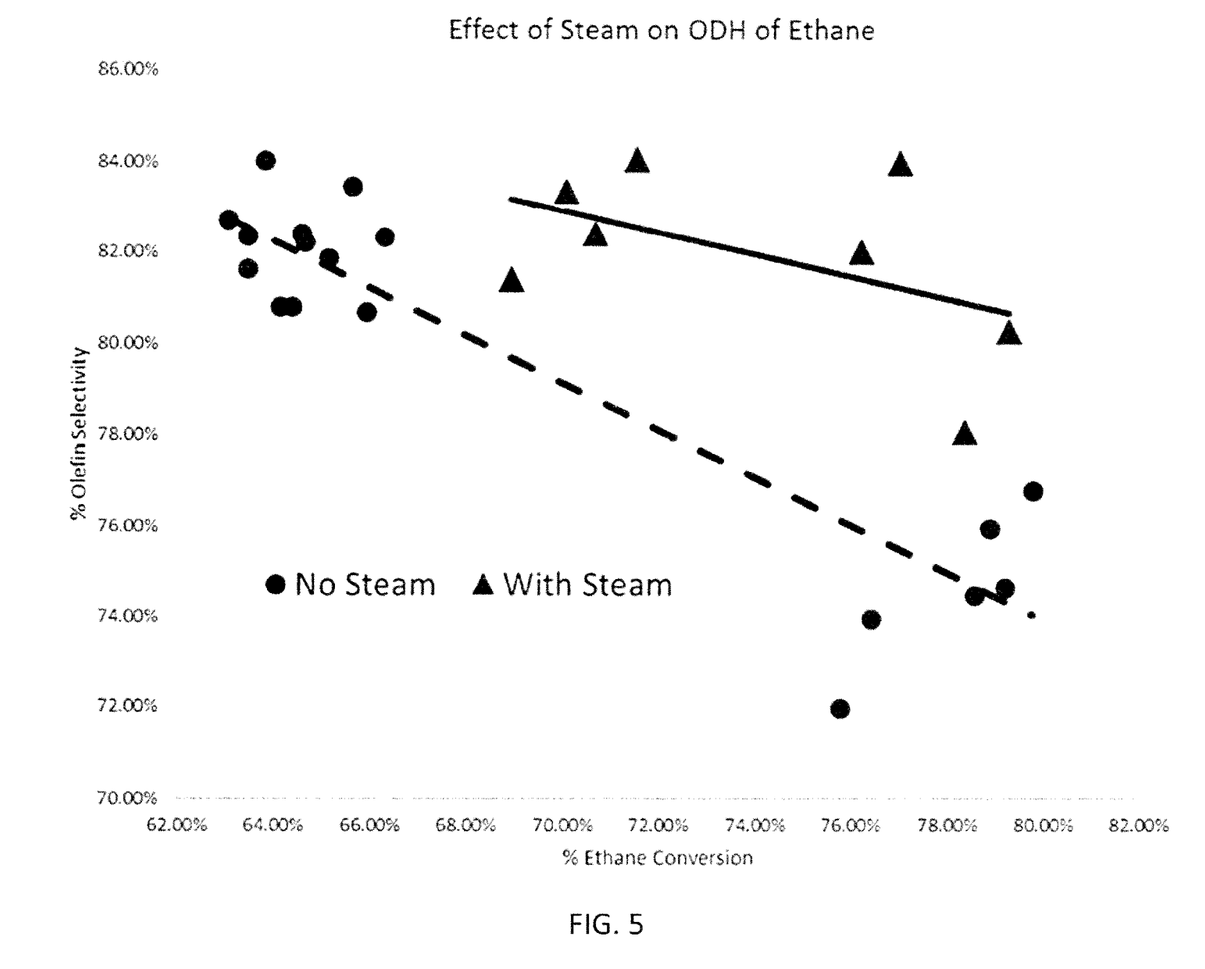
FIG. 5 is a graph illustrating the effect of steam on the oxidative dehydrogenation of ethane in accordance with aspects of the invention.

A 10 ml sample of a spray-dried oxygen transfer agent formed of lithium, boron, manganese oxides, magnesia oxides and other binders was charged to a ¾ inch inner diameter alumina reactor and fed from bottom to top as a fluid bed. The oxidative dehydrogenation of a hydrocarbon feed was conducted at a temperature of 825° C. to 840° C. at a gas hourly space velocity ("GHSV") of 2,400-4,800 hr−1. Ethane was employed as the hydrocarbon feed and the product included ethylene, propylene, butylenes, C5+ olefins, and aromatic compounds. The ethane cycle lasted for 15 seconds followed by 2 minutes of nitrogen, 10 minutes of air, 2 minutes of nitrogen after which another ethane charge was made. The results of these experimental runs over 165 cycles are shown in FIG. 5. The first 149 cycles did not include a steam feed. The final 16 cycles included a one to one mole ratio of steam (via a water injection system) to ethane as the feed to the fluid bed reactor. FIG. 5 illustrates that the addition of steam increases the activity of ethane conversion and selectivity to ethylene and other olefin products as well as an increase in the overall yield of desired olefin products.

Example 2

In this example, pressure was applied during the oxidative dehydrogenation of an ethane feed for the production of an olefin stream. Table 1, provided below, demonstrates the significant increase in the rate of conversion due to an increase in the pressure applied during oxidative dehydrogenation of the ethane feed stream. In each experimental run, the oxygen transfer agent was a mixed ionic electronic conducting material containing a metal oxide comprised of Li, Mn, B, Mg and O and the temperature was held at 840° C.

TABLE 1

| Effect of Pressure on Rate | | | | |
|---|---|---|---|---|
| Absolute Pressure psia. | GHSV, hr$^{-1}$ | % C$_2$ Conversion | % C$_2^+$ Selectivity | Rate mol-C$_2$/ g-cat.-sec. |
| 15 | 4,800 | 85 | 85 | 0.00005 |
| 115 | 100,500 | 30 | 95 | 0.00037 |

As shown in above, the conversion rate increased by a factor of 7.44 while the pressure increased by a factor of 7.66, suggesting that the reaction of the oxygen transfer agent with hydrogen is a first order reaction in hydrogen. Surprisingly, the selectivity to the desired product, ethylene and other olefins, also increased with pressure.

Figure 6:
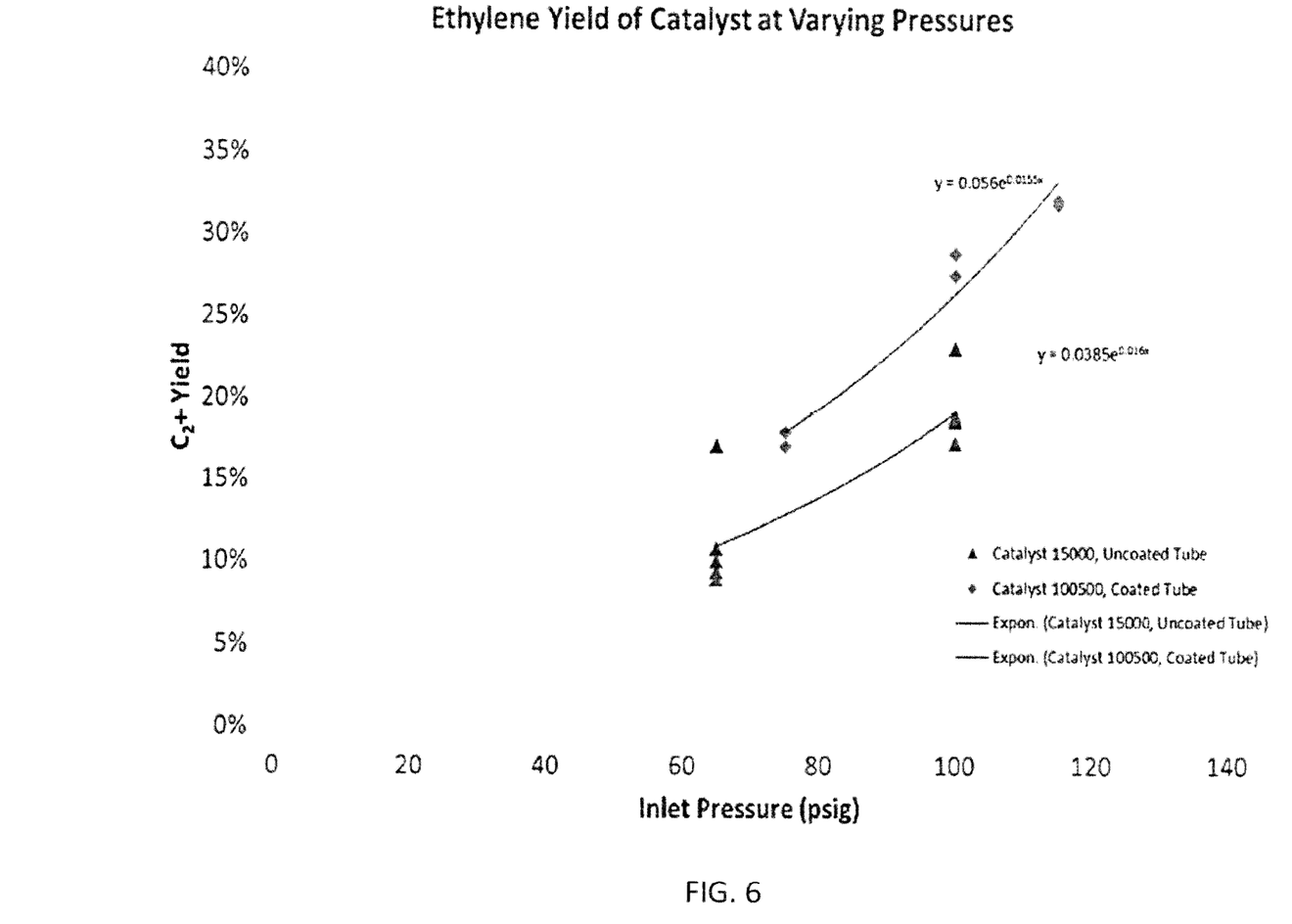
FIG. 6 is a graph illustrating the effect of pressure on the oxidative dehydrogenation of ethane according to aspects of the invention.

The beneficial effect of increasing the pressure over a range of 65 psig to 115 psig is illustrated in FIG. 6. The experimental runs illustrated by the graph of FIG. 6 were carried out in both uncoated 310 SS and aluminized 310 SS reactors. Additionally, the space time yield of desired products increases with pressure.

Figure 7:
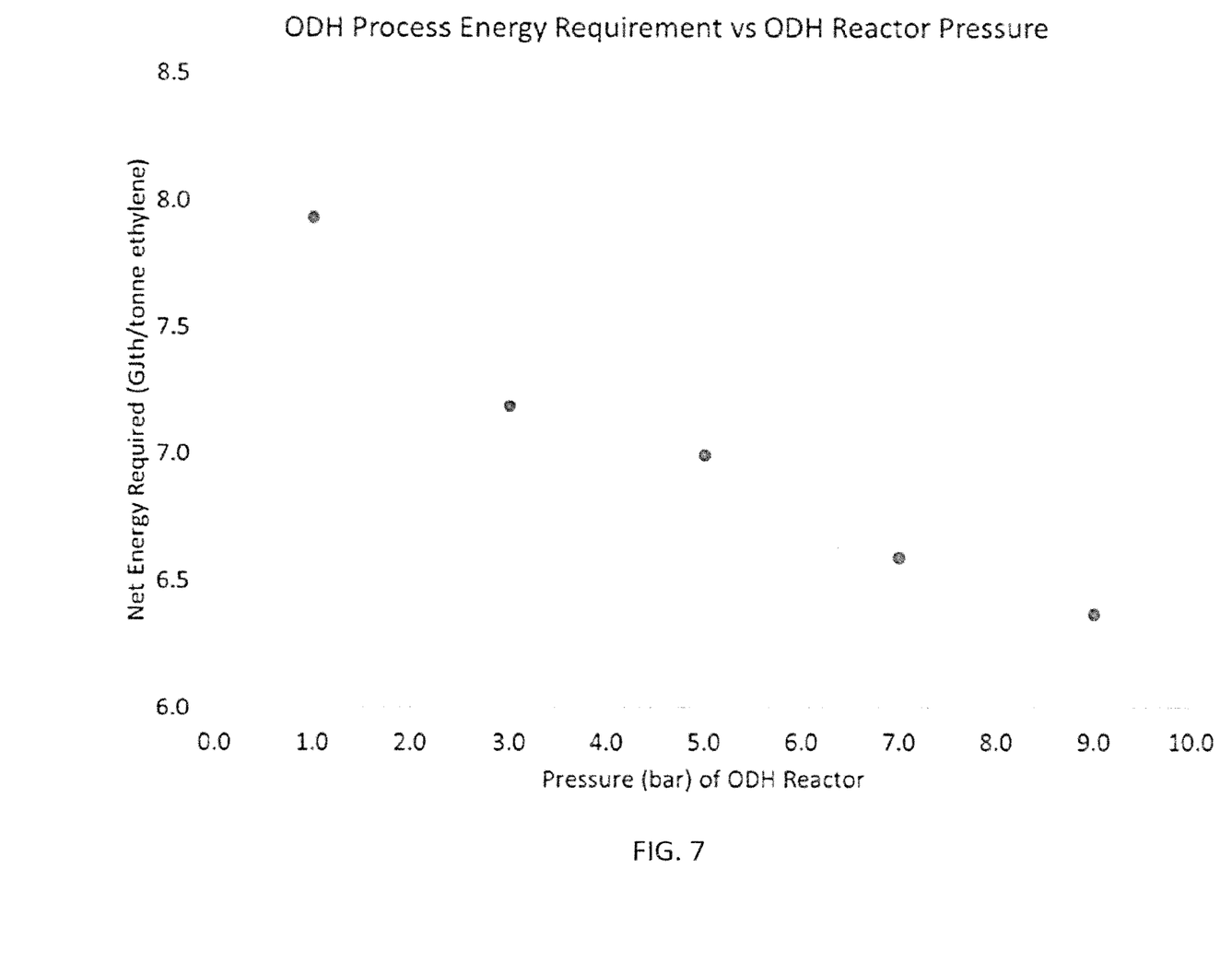
FIG. 7 is a graph illustrating the effect of increased pressure during oxidative dehydrogenation of ethane on the energy utilization of a system in accordance with aspects of the invention.

A majority of the capital cost of an ethylene plant, whether steam cracking or oxidative dehydrogenation, is the product recovery and recycle section of the plant. The beneficial effect of lowering the overall process energy utilization by operating an oxidative dehydrogenation process at superatmospheric pressure can be seen from the summary of process simulations shown in FIG. 7. These simulations assumed a constant ethane conversion and ethylene yield. This would be accomplished in practice by modifying the oxidative dehydrogenation reactor feed space velocity and temperature to obtain the optimal yields.

Example 3—Prophetic

In this prophetic example, an oxygen transfer agent is prepared by ball milling manganese dioxide (32.2 grams), boric acid (11.3 grams), magnesia (42.3 grams) and lithium hydroxide (4.5 grams) with water. The milled mixture is calcined in air at 900° C. for 8 hours. A sample (e.g., 5 ml) of the oxygen transfer agent is charged to a ½ inch inner diameter alumina reactor. Oxidative dehydrogenation conversions are simulated at 840° C. at GHSVs of 4,800 hr−1 based on the dry ethane feed. Ethane may be used to produce the ethylene-containing product, which would also include propylene, butylenes, C5+ olefins, and aromatic compounds. The sum of these products define the C2+ selectivity. The ethane cycle is simulated as running for 15 seconds followed by 2 minutes of nitrogen, 10 minutes of air, 2 minutes of nitrogen after which another ethane charge is made. The results of the simulated runs are projected in Table 2, shown below.

TABLE 2

Effect of Pressure and Steam on Oxidative Dehydrogenation Rate

| Absolute Pressure, psia | Additional Steam, mol $H_2O$/mol $C_2$ | GHSV, $hr^{-1}$ | % $C_2$ Conversion | % $C_2^+$ Selectivity | Rate mol-$C_2$/g-cat.-sec. |
|---|---|---|---|---|---|
| 15 | No Steam | 4,800 | 85 | 85 | 0.00005 |
| 115 | No Steam | 100,500 | 30 | 95 | 0.00037 |
| 15 | 1 | 4,800 | 90 | 87 | 0.00006 |
| 115 | 1 | 100,500 | 40 | 95 | 0.00049 |

Although the invention is illustrated and described herein with reference to specific embodiments, the invention is not intended to be limited to the details shown. Rather, various modifications may be made in the details within the scope and range of equivalents of the claims and without departing from the invention. Numerous variations, changes and substitutions will occur to those skilled in the art without departing from the spirit of the invention. Accordingly, it is intended that the appended claims cover all such variations as fall within the spirit and scope of the invention.

What is claimed is:

1. A method for producing one or more olefins from a hydrocarbon feed comprised of one or more alkanes, the method comprising:
   contacting a hydrocarbon feed comprising at least one alkane and a steam feed with an oxygen transfer agent under a pressure of 50 bar to 800 bar to produce at least one olefin, the oxygen transfer agent comprising a metal oxide that acts as an oxidizing agent to oxidize the at least one alkane, wherein during the contacting step the hydrocarbon feed has a temperature of 825° C. to 1100° C. and a molar ratio of water in the steam feed to the hydrocarbon feed is from 1:10 to 10:1; and
   collecting a product stream comprising the at least one olefin and water;
   wherein the metal oxide is reduced and provides the oxygen in the water.

2. The method of claim 1, wherein an increase in the pressure increases the selectivity for olefins.

3. The method of claim 1, wherein the metal oxide comprises at least one element selected from the group consisting of Na, Li, Ca, Mg, Sr, P, and Ba.

4. The method of claim 1, where the metal oxide comprises at least one metal oxide selected from the group consisting of oxides of La, Ce, Pr, Tb, Nd, Mn, W, Ti, Fe, and Dy.

5. The method of claim 1, wherein the metal oxide is in combination with a zeolite.

6. A method for producing one or more olefins from a hydrocarbon feed comprised of one or more alkanes, the method comprising:
   contacting a hydrocarbon feed comprising at least one alkane and a steam feed with an oxygen transfer agent under a pressure of 50 bar to 800 bar and at a gas hourly space velocity of from 4800 $hr^{-1}$ to 100,500 $hr^{-1}$ to produce at least one olefin, the oxygen transfer agent comprising a metal oxide that acts as an oxidizing agent to oxidize the at least one alkane, wherein during the contacting step the hydrocarbon feed has a temperature of 900° C. or more and a molar ratio of water in the steam feed to the hydrocarbon feed is from 1:10 to 10:1; and
   collecting a product stream comprising the at least one olefin and water,
   wherein during the contacting step the metal oxide is reduced and provides the oxygen in the water.

* * * * *